United States Patent [19]

Mod et al.

[11] 4,092,319

[45] May 30, 1978

[54] SULFUR-CONTAINING ANTIMICROBIAL ESTER-AMIDES

[75] Inventors: Robert R. Mod, New Orleans; Frank C. Magne, Metairie; Gene Sumrell, New Orleans; Arthur F. Novak, Baton Rouge, all of La.

[73] Assignee: The United States of America as represented by the Secretary of Agriculture, Washington, D.C.

[21] Appl. No.: 833,882

[22] Filed: Sep. 16, 1977

Related U.S. Application Data

[62] Division of Ser. No. 737,457, Nov. 1, 1976, Pat. No. 4,061,634.

[51] Int. Cl.$^2$ ........................................... C07D 295/18
[52] U.S. Cl. ................................................. 260/293.85
[58] Field of Search .................................... 260/293.85

[56] References Cited

U.S. PATENT DOCUMENTS

| 3,340,147 | 9/1967 | Martin et al. | 260/293.85 |
| 4,035,492 | 7/1977 | Kalopissis et al. | 260/293.85 |

*Primary Examiner*—Henry R. Jiles
*Assistant Examiner*—R. W. Ramsuer
*Attorney, Agent, or Firm*—M. Howard Silverstein; David G. McConnell; Salvador J. Cangemi

[57] ABSTRACT

Sulfur-containing long chain fatty ester-amides have been prepared by the addition of mercaptoacetic acid to the terminal and nonterminal double bonds of unsaturated amides followed by esterification of the carboxyl group with the appropriate alcohol. These compounds exhibit antimicrobial activity and have properties making them useful as antimicrobial agents.

2 Claims, No Drawings

SULFUR-CONTAINING ANTIMICROBIAL ESTER-AMIDES

This is a division of application Ser. No. 737,457 filed 11/1/76, now U.S. Pat. No. 4,061,634.

BACKGROUND OF THE INVENTION

(1) Field of the Invention

This invention relates to certain new sulfur-containing organic compounds which have exhibited antimicrobial activity. More particularly, this invention relates to reaction products of mercaptoacetic acid with N,N-disubstituted long chain aliphatic amides.

(2) Description of the Prior Art

It is known to the art that a variety of N-substituted fatty amides show antimicrobial activity. However, many are not antimicrobially active and there is a wide difference in the activity of those which are active. Some are active against only one, or a small number of microorganisms, while others show a broad spectrum of activity against many types of organisms. Testing must be done in the specific application wanted to determine whether a given antimicrobial agent will be useful for that application.

SUMMARY OF THE INVENTION

Thirteen sulfur-containing ester-amides, which fall into two general categories, are disclosed. These ester-amides were prepared by the addition of mercaptoacetic acid to the double bonds of unsaturated fatty amides, followed by esterification. These new compounds inhibit growth of microorganisms that include bacteria, yeast, and molds.

The compounds which are the products of this invention are of the following general structures:

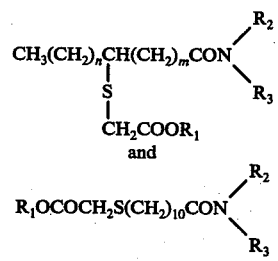

where $R_1$ is a lower alkyl or alkenyl group of 1 to 6 carbons; $R_2$ and $R_3$ may be the same or different and are alkyl or alkoxyalkyl groups, or may join to form a morpholine or piperidine ring system, $n + m = 15$ and $n = m \pm 1$.

DESCRIPTION OF THE PREFERRED EMBODIMENTS

The compounds which are the products of this invention are prepared by conventional laboratory procedures involving thermal addition of mercaptoacetic acid to terminal and non-terminal double bonds of unsaturated N,N-disubstituted fatty amides, followed by esterification of the carboxyl group with a lower saturated or unsaturated alcohol containing one to six carbons. The acyl component of the amide may be a normal, branched, or substituted alkenoic group containing from 11 to 22 carbon atoms, and the amide nitrogen is derived from a dialkylamine, an alkyl-alkoxy-alkylamine, a dialkoxyalkylamine, or a nitrogen heteroalicyclic. Typical amines are dibutylamine, 4-methylpiperidine, diethoxyethylamine, and morpholine.

The bioactivity of these various new sulfur-containing compounds has been established by us in vitro but, as will be apparent to those skilled in the arts pertaining to the growth inhibition of bacteria, yeasts and molds, the compounds, besides being used as such, will for utilitarian purposes commonly be formulated using a diluent that can be either liquid, viscous, or solid.

A wide variety of extending agents is operable, the only significant requirement being that the diluent or extender be inert with respect to the compound involved. Petroleum jellies, various alcohols and polyols, vegetable oils and the like are suitable. The microorganisms used were obtained from stock cultures. Difco Dehydrated Mycological Agar at pH 7.0 was used to test the inhibition of the test organisms by the compounds being screened. Suspensions of the test organisms were prepared by transferring a loop of spores into sterile saline. Hardened agar plates were inoculated by placing 3 drops of the suspension onto the agar. The microorganisms were spread over the surface of the plates with sterile glass rods. These plates were employed in the activity estimation against microbial growth. Filter paper discs 6.5 mm in diameter, made from Whatman Number 1 filter paper were used to evaluate the compounds. The paper discs wetted until they were completely saturated with the test compound and were placed on the surface of the agar plates inoculated with the test organisms. To eliminate any errors which could result from an insufficient number of tests, a minimum of three experiments, at different times, employing duplicates plates were made for each compound under test. All plates were incubated at the optimum growing temperatures for each organism and the readings were taken after 24, 48, 72, and 120 hour periods.

The organisms used in the tests were *Candida albicans*, *Staphylococcusaureus*, *Escherichia coli*, and *Aspergillus species*. They were obtained from stock cultures. The data from these tests are tabulated in Table I.

Specific examples showing the preparation of each of the new compounds being claimed are set forth below along with appropriate data in tabular form which is being submitted for the purpose of establishing the growth inhibiting properties of the claimed compounds.

TABLE I
ANTIMICROBIAL ACTIVITY OF SULFUR-CONTAINING FATTY AMIDES

| Compund | Antimicrobial Activity [a] Microorganisms [b] | | | |
|---|---|---|---|---|
| | A | B | C | D |
| 1. 9(10)-(Carbomethoxymethylthio)stearoylmorpholine | ++ | + | + | ++ |
| 2. 9(10)-(Carbethoxymethylthio)stearoylmorpholine | ++ | 0 | + | ++ |
| 3. 9(10)-(Carbopropoxymethylthio)stearoylmorpholine | 00 | 00 | + | ++ |
| 4. 9(10)-(Carbopentoxymethylthio)stearoylmorpholine | 00 | 0 | 00 | 00 |
| 5. 9(10)-(Carbo-3-methyl-1-butoxymethylthio)stearoylmorpholine | + | 0 | 00 | + |
| 6. 9(10)-(Carbohexoxymethylthio)stearoylmorpholine | 0 | 0 | 00 | ++ |
| 7. 9(10)-(Carballyloxymethylthio)stearoylmorpholine | + | + | 00 | + |
| 8. N,N-Bis(2-ethoxyethyl)-9(10)-(carbethoxymethylthio)stearamide | ++ | 0 | 00 | 0 |

TABLE I-continued

ANTIMICROBIAL ACTIVITY OF SULFUR-CONTAINING FATTY AMIDES

| Compund | Antimicrobial Activity [a] Microorganisms [b] | | | |
|---|---|---|---|---|
| | A | B | C | D |
| 9. N,N-Bis(2-ethoxyethyl)-9(10)-(carbo-3-methyl-1-butoxymethylthio)stearamide | 0 | 0 | 00 | 0 |
| 10. N,N-Dibutyl-9(10)-(carbo-3-methyl-1-butoxymethylthio)stearamide | 00 | 00 | 0 | + |
| 11. N-Methyl-N-butyl-9(10)-(carbo-3-methyl-1-butoxymethylthio)stearamide | 00 | 00 | 00 | 0 |
| 12. 9(10)-(Carbethoxymethylthio)stearoyl-4-methylpiperidine | ++ | + | + | ++ |
| 13. 11-(Carbethoxymethylthio)undecanoylmorpholine | 0 | 00 | 00 | 00 |

[a]++ = The zone of inhibition was at least 0.5 cm beyond disc at 120 hrs
+ = The zone of inhibition was less than 0.5 cm beyond disc at 120 hrs
00 = Organism failed to grow on disc at 120 hrs
0 = Slight growth on the saturated disc at 120 hrs
[b]A = Candida albicans;
B = Staphylococcus aureus;
C = Escherichia coli;
D = Aspergillus species

EXAMPLE 1

9(10)-(Carbomethoxymethylthio)stearoylmorpholine

A. 9(10)-Carboxymethylthio)stearoylmorpholine 158 g (0.44 mole) of N-oleoylmorpholine and 124.5 g (1.35 mole) of mercaptoacetic acid were placed in a flask equipped with stirrer. The temperature was raised to 90° C, after which the reaction was continued for two hours. The excess mercaptoacetic acid was removed by distillation followed by water washings. Unreacted N-oleoylmorpholine was removed by the urea complex procedure. NMR spectra indicated unsaturation was completely removed.

B. 9(10)-Carbomethoxymethylthio)stearoylmorpholine 10 g (0.02 mole) of 9(10)-(carboxymethylthio)-stearoylmorpholine, 3.8 g (0.12 mole) of methyl alcohol, 0.1 g of 2-naphthalenesulfonic acid and benzene were placed in a flask equipped with reflux condenser and Dean-Stark trap. The temperature was raised until reflux was achieved and then continued for a period of eight hours or until water had ceased to be azeotroped. The mixture was cooled, dissolved in benzene, washed with water, dried over anhydrous sodium sulfate, filtered and passed through a column of activated alumina to remove any free acid. The benzene fraction was discarded and the alcohol fraction retained. The solvent was removed by stripping at reduced pressure. The product, 9(10)-carbomethoxymethylthio)stearoylmorpholine, had a nitrogen content of 3.06% (theory, 3.06%).

EXAMPLE 2

9(10)-(Carbethoxymethylthio)stearoylmorpholine

This compound was prepared by the procedure of Example 1 from 10 g (0.02 mole) of 9(10)-(carboxymethylthio)stearoylmorpholine and 3.2 g (0.07 mole) of ethyl alcohol. The product, 9(10)-(carbethoxymethylthio)stearoylmorpholine, had a nitrogen content of 3.06% (theory, 2.97%).

EXAMPLE 3

9(10)-(Carbopropoxymethylthio)stearoylmorpholine

This compound was prepared by the procedure of Example 1 from 10 g (0.02 mole) of 9(10)-(carboxymethylthio)stearoylmorpholine and 4.2 g (0.07 mole) of propyl alcohol. The product, 9(10)-(carbopropoxymethylthio)stearoylmorpholine had a nitrogen content of 2.83% (theory, 2.88%).

EXAMPLE 4

9(10)-(Carbopentoxymethylthio)stearoylmorpholine

This compound was prepared by the procedure of Example 1 from 10 g (0.02 mole) of 9(10)-(carboxymethylthio)stearoylmorpholine and 6.2 g (0.07 mole) of pentyl alcohol. The product, 9(10)-(carbopentoxymethylthio)stearoylmorpholine had a nitrogen content of 2.77% (theory, 2.72%).

EXAMPLE 5

9(10)-(Carbo-3-methyl-1-butoxymethylthio)stearoylmorpholine

This compound was prepared by the procedure of Example 1 from 10 g (0.02 mole) of 9(10)-(carboxymethylthio)stearoylmorpholine and 6.2 g (0.07 mole) of isoamyl alcohol. The product, 9(10)-(carbo-3-methyl-1-butoxymethylthio)stearoylmorpholine, had a nitrogen content of 2.65%) (theory, 2.72%).

EXAMPLE 6

9(10)-(Carbohexoxymethylthio)stearoylmorpholine

This compound was prepared by the procedure of Example 1 from 10 g (0.02 mole) of 9(10)-(carboxymethylthio)stearoylmorpholine and 7.1 g (0.07 mole) of hexyl alcohol. The product, 9(10)-(carbohexoxymethylthio)stearoylmorpholine, had a nitrogen content of 2.43% (theory, 2.65%).

EXAMPLE 7

9(10)-(Carballyloxymethylthio)stearoylmorpholine

This compound was prepared by the procedure of Example 1 from 10 g (0.02) mole of 9(10)-(carboxymethylthio)stearoylmorpholine and 4.1 g (0.07 mole) of allyl alcohol. The product, 9(10)-(carballyloxymethylthio)stearoylmorpholine had a nitrogen content of 2.96% (theory, 2.90%).

EXAMPLE 8

N,N-Bis(2-ethoxyethyl)-9(10)-(carbethoxymethylthio)-stearamide

This compound was prepared by the procedure of Example 1 from 10 g (0.02 mole) of N,N-bis(2-ethoxyethyl)-9(10)-(carboxymethylthio)stearamide and 2.8 g (0.06 mole) of ethyl alcohol. The product, N,N-bis(2-ethoxyethyl)-9(10)-(carbethoxymethylthio)stearamide, had a nitrogen content of 2.69% (theory, 2.57%).

EXAMPLE 9

N,N-Bis(2-ethoxyethyl)-9(10)-(carbo-3-methyl-1-butoxymethylthio)stearamide

This compound was prepared by the procedure of Example 1 from 10 g (0.02 mole) of N,N-bis(2-ethoxyethyl)-9(10)-(carboxymethylthio)stearamide and 5.3 g (0.06 mole) of isoamyl alcohol. The product, N,N-bis(2-ethoxyethyl)-9(10)-(carbo-3-methyl-1-butoxymethylthio)stearamide had a nitrogen content of 2.37% (theory, 2.38%).

EXAMPLE 10

N,N-Dibutyl-9(10)-(carbo-3-methyl-1-butoxymethylthio)stearamide

This compound was prepared by the procedure of Example 1 from 10 g (0.02 mole) of N,N-dibutyl-9(10)-(carboxymethylthio)stearamide and 5.3 g (0.06 mole) of isoamyl alcohol. The product, N,N-dibutyl-9(10)-(carbo-3-methyl-1-butoxymethylthio)stearamide, had a nitrogen content of 2.47%, (theory 2.52%).

EXAMPLE 11

N-Methyl-N-butyl-9(10)-(carbo-3-methyl-1-butoxymethylthio)stearamide

This compound was prepared by the procedure of Example 1 from 10 g (0.02 mole) of N-methyl-N-butyl-9(10)-(carboxymethylthio)stearamide and 5.3 g (0.06 mole) of isoamyl alcohol. The product, N-methyl-N-butyl-9(10)-(carbo-3-methyl-1-butoxymethylthio)-stearamide, had a nitrogen content of 2.53% (theory, 2.73%).

EXAMPLE 12

9(10)-(Carbethoxymethylthio)stearyl-4-methylpiperidine

This compound was prepared by the procedure of Example 1 from 6 g (0.01 mole) of 9(10)-(carboxymethylthio)stearoyl-4-methylpiperidine and 2.8 g (0.06 mole) of ethyl alcohol. The product, 9(10)-(carbethoxymethylthio)stearoyl-4-methylpiperidine, had a nitrogen content of 2.56% (theory, 2.90%).

EXAMPLE 13

11-(Carbethoxymethylthio)undecanoylmorpholine

A. 11-(carboxymethylthio)undecanoylmorpholine 5 g (.02 mole) of 10-undecenoylmorpholine and 2.3 g (.025 mole) of mercaptoacetic acid were placed in a flask equipped with stirring bar. The temperature was raised to 60° C and maintained there for two hours with stirring. The excess mercaptoacetic acid was removed by distillation at reduced pressure and water washings.

B. 11-(Carbethoxymethylthio)undecanoylmorpholine 6 g (0.017 mole) of 11-(Carboxymethylthio)undecanoylmorpholine, 4.8 g (0.11 mole) of anhydrous ethyl alcohol and 1 g of 2-naphthalenesulfonic acid were placed in a flask equipped with reflux condenser, and refluxed for 16 hours. The mixture was dissolved in benzene, washed with water, dried over anhydrous sodium sulfate, filtered, passed through a column of activated alumina and stripped of solvent. The product, 11-(carbethoxymethylthio)undecanoylmorpholine, had a nitrogen content of 3.66% (theory, 3.75%).

We claim:

1. A sulfur-containing ester amide having antimicrobial activity and the general structure:

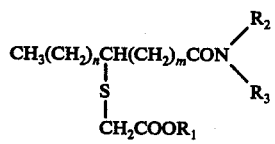

where $R_1$ is a lower alkyl or alkenyl group; $R_2$ and $R_3$ cojointly form a piperidine ring; $n + m$ add up to 15 and $n = m$ plus or minus 1.

2. The ester amide of claim 1 wherein the compound is 9(10)-(carbethoxymethylthio)stearoyl-4-methylpiperidine.